United States Patent
Behrend

[19]

[11] Patent Number: 5,947,736
[45] Date of Patent: Sep. 7, 1999

[54] OCCLUSAL REGISTRATION COPING SYSTEM

[76] Inventor: Donald Albert Behrend, 46 Carters Avenue, Toorak, Victoria 3142, Australia

[21] Appl. No.: 09/085,291

[22] Filed: May 27, 1998

[30] Foreign Application Priority Data

Jun. 2, 1997 [AU] Australia .................................. PO7151

[51] Int. Cl.[6] .................................................... A61L 9/00
[52] U.S. Cl. ........................................... 433/214; 433/172
[58] Field of Search .................................... 433/172, 173, 433/174, 175, 176, 213, 214

[56] References Cited

U.S. PATENT DOCUMENTS

| | | | |
|---|---|---|---|
| 4,767,331 | 8/1988 | Hoe | 433/213 |
| 4,856,994 | 8/1989 | Lazzara et al. | 433/173 |
| 5,108,288 | 4/1992 | Perry | 433/173 |
| 5,114,343 | 5/1992 | Musikanti et al. | 433/173 |
| 5,116,225 | 5/1992 | Riera | 433/173 |
| 5,564,924 | 10/1996 | Kwan | 433/173 |
| 5,662,473 | 9/1997 | Rassoli et al. | 433/172 |
| 5,674,071 | 10/1997 | Beaty et al. | 433/172 |

*Primary Examiner*—John J. Wilson
*Assistant Examiner*—Patrick A. Hilsmier
*Attorney, Agent, or Firm*—Ryan Kromholz & Manion

[57] ABSTRACT

An occlusal registration coping (10) having a base member (11) adapted to be attached by an integral screw (13) to an implant within the jaw or to an implant abutment, and a head member (12). The base member and the head member being detachably connected together, by ridges or ribs (19) which interlock with grooves or indentations (16) and formed around a projection (15) on the base member and around the inside of a matching socket (18) in the head member. The end of the base member remote from the implant or abutment to which it is adapted to be attached contains a socket (17) of hexagonal cross-sectional shape and adapted to receive a tool of matching cross-section whereby the base member can be screwed into the implant or abutment to form a screw connection therebetween. A set of copings may be provided comprising a plurality of different base members and a plurality of color coded head members of different lengths.

11 Claims, 1 Drawing Sheet

OCCLUSAL REGISTRATION COPING SYSTEM

TECHNICAL FIELD

The present invention relates to an occlusal registration roping system for use in dental procedures involving the replacement of missing teeth by means of implants.

BACKGROUND ART

The construction of a dental restoration on what are referred to as osseointegrated implants requires the articulation of maxillary and mandibular casts. In most cases involving several missing teeth this is accomplished by means of one or more occlusal registrations with a wax or elastomeric material and, possibly, a facebow recording with a bitefork.

At present, there is no component or device available which is specifically designed to support the occlusal registration material or facebow bitefork over the area containing the implants. The current practice is to use a component designed for another purpose, such as an impression coping, which may not be of satisfactory size, particularly in relation to its height or length, for a particular situation. An alternative is to construct a custom-made platform, which is a time-consuming procedure.

DISCLOSURE OF THE INVENTION

It is an object of the present invention to provide copings designed to support the occlusal registration material or facebow bitefork over the area containing the implants.

In its broadest aspect the invention comprises a coping system having at least one base member adapted to be attached to an implant within the jaw or to an implant abutment, and a plurality of head members of different lengths, each, said base member being, detachably connected in use, to any selected one of said head members.

BRIEF DESCRIPTION OF THE DRAWINGS

Several preferred embodiments of the invention will now be described with reference to the accompanying drawings, in which.

BEST MODES FOR CARRYING OUT THE INVENTION

With each preferred embodiment of the invention, the occlusal registration coping generally indicated as 10 is approximately cylindrical in shape and has a base member 11 of titanium or other suitable material which is designed to be attached to an implant or an intervening implant abutment and a domed head member 12 which acts as a platform to support the registration material or facebow bitefork. The domed head 12 may be smooth or may have one or more concentric grooves on its surface. The diameter of the head 12 is larger than that of an impression coping or an abutment, due to the different purpose of such items. The comparatively large area and the curvature of the surface or the head enables it to function as a platform for the registration material or bitefork even when the implant is tilted or placed outside the line of the dental arch.

In the preferred embodiments of the invention, the copings 10 are made available in various models, each with a base designed to be attached to a particular type of implant or implant abutment.

Figure 1:
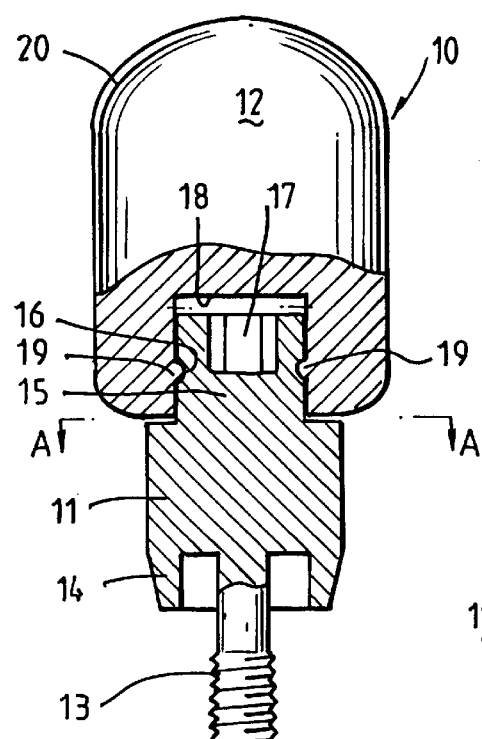
FIG. 1 is a side elevational view of a first preferred embodiment of the invention.
Figure 1A:
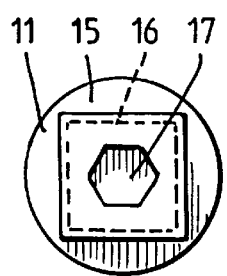
FIG. 1A is a plan view taken along line A—A of FIG. 1.
Figure 2:
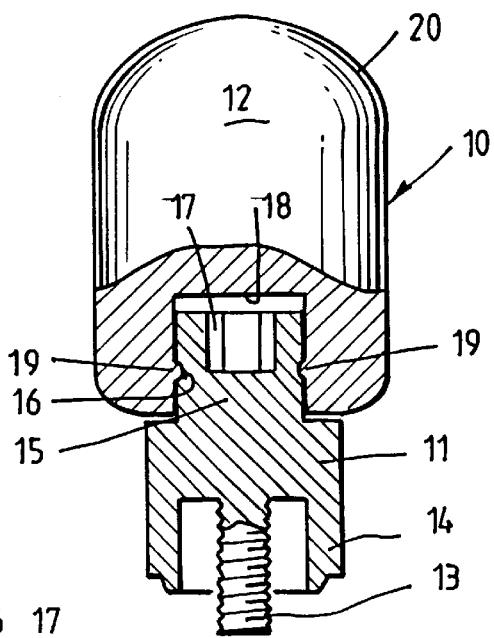
FIG. 2 is a side elevational view of a second preferred embodiment of the invention.
Figure 3:
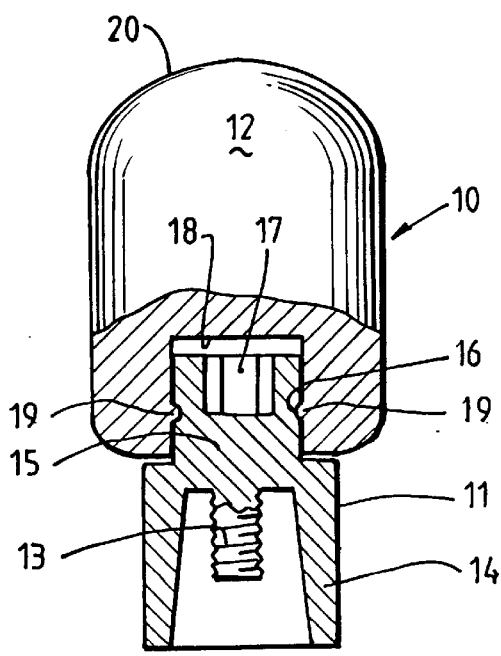
FIG. 3 is a side elevational view of a third preferred embodiment of the invention.
Figure 4:
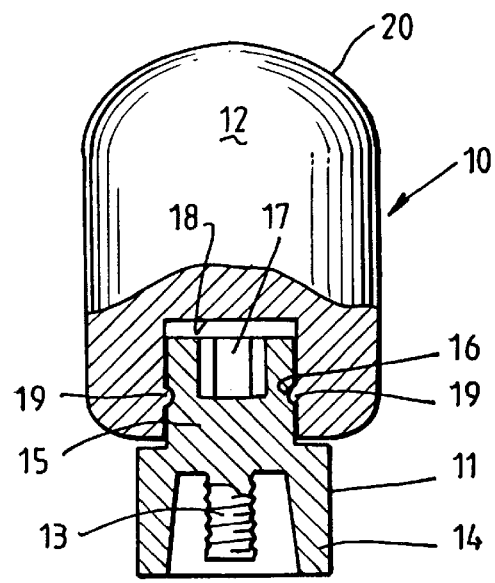
FIG. 4 is a side elevational view of a fourth preferred embodiment of the invention.

The preferred embodiments illustrated are all copings for use with the Branemark System manufactured by Nobel Biocare. FIG. 1 shows an occlusal registration coping adapted to be attached to an implant. The base component 11 has at one end a central screw 13 and a rim 14 of annular cross-section similar to those on the Branemark System healing abutment. The opposite end of the base component has, with reference to FIG. 1A a projection 15 of square cross-section with aligned grooves or indentations 16 along each side. Formed in the end of the square projection is a hexagonal shaped socket 17 to accommodate a standard Branemark System screwdriver. This allows the base member 11 to be attached to or removed from an implant in a similar manner to that of a Branemark System healing abutment using either a manual screwdriver or machine driven screwdriver. The base-member for the implant may be made in three forms, to match Regular Platform, Wide Platform and Narrow Platform implants, but each form will accept the same head member 12. The head member 12 may be made of a moulded plastic, and has in one and a socket 18 of square cross-section which matches and fits over the square projection 15 on the base 11. Ridges or ribs 19 within the square socket 18 engage the grooves or indentations 16 in the square projection 15 of the base, providing a "snap" fit. As an alternative the head and base members may be connected by screwed connections. The opposite end of the head member 12 hag a domed surface 20 which may be smooth or may have a series of concentric grooves. The head components are made in a range of heights or lengths which may be identified by different colours. FIG. 2 shows an occlusal registration coping to be attached to a standard abutments FIG. 3 shows an occlusal registration coping to be attached to an Estheticone abutment or a 17° Angulated abutment; and FIG. 4 shows an occlusal registration coping to be attached to a Miruscone abutment. The base member of each of these copings has a central screw and a circular rim similar to those on the corresponding Branemark system tapered impression coping. The opposite ends of the base members are similar to that described for the base components which attach to the implants, and hence the same head members can be used with all types or base members.

Slight modifications of the designs of the base members can be made for use of the occlusal registration copings with other implant systems.

The occlusal registration and/or facebow recording is generally taken at the dental appointment when the impresiions are made. The occlusal registration coping base members are screwed into one or more of the implants or abutments of which the impression was taken. The head member is then attached to each base component to form a complete coping. The height or length of each head member should be selected go that the coping is slightly short of the opposing teeth when the jaws are in occlusion, and therefore in accordance with the present invention the lengths of each of the head members is different to suit different situations. The centric registration is then recorded with an elastomeric or wax material. If required, eccentric registrations and a facebow recording may also be taken with the copings in place.

The occlusal registration coping or copings are then removed and either sent to the dental laboratory or their lengths (as identified, for example, by the colour of the head component) recorded and indicated to the dental technician. The same or similar copings are attached to the corresponding implant replicas or abutment replicas on the cast, which can then be mounted using the registrations.

It will be understood that many modifications may be made in the design or materials of an Occlusal Registration Coping System in accordance with the invention and all such modifications which come within the scope of the invention shall be deemed to be within the ambit of the description in this document.

I claim:

1. An occlusal registration coping system having at least one base member adapted to be attached to an implant within the jaw or to an implant abutment, and a plurality of head members of different lengths, said at least one base member being selectively detachably connected, to form an occlusal registration location for the implant to each of said head members.

2. A coping system as claimed in claim 1 wherein the at least one said base includes a projection and the head members include a matching socket to said projection.

3. A coping system as claimed in claim 2 wherein the at least one said base member and said head members are detachably connected together by ridges or ribs which interlock with grooves or indentations and which are formed around the projection on said base member or around the inside of the matching socket in said head members.

4. A coping system as claimed in claim 3 wherein the ridges or ribs are formed around the inside of the socket in said head member and the grooves or indentations are formed around the projection on said base member.

5. A coping system as claimed in claim 2 wherein the matching projection and socket are of polygonal cross-section.

6. A coping system as claimed in claim 5 wherein the matching projection and socket are of square cross-section.

7. A coping system as claimed in claim 1 wherein the end of the at least one said base member remote from the implant or abutment to which the base member is adapted to be attached contains a socket of predetermined cross-section which is shaped and adapted to receive a tool of matching cross-section whereby the base member may, in use, be screwed into the implant or abutment to form a screw connection there between.

8. A coping system as claimed in claim 1 wherein the at least one base member is formed to match various configurations of implants or abutments.

9. A coping system as claimed in claim 1 wherein each said head member has a domed shaped surface of relatively large area.

10. A coping system as claimed in claim 1 wherein the diameters of said head members are larger than that of an impression coping or an abutment.

11. A set of copings as claimed in claim 10 wherein the head members are color coded in accordance with their particular length.

* * * * *

UNITED STATES PATENT AND TRADEMARK OFFICE
CERTIFICATE OF CORRECTION

PATENT NO. : 5,947,736  
DATED : September 7, 1999  
INVENTOR(S) : Donald A. Behrend Page 1 of 1

It is certified that error appears in the above-identified patent and that said Letters Patent is hereby corrected as shown below:

Column 1,
Line 6, delete "roping" and substitute -- coping --
Line 37, delete the commas (,) after "each" and "being"

Column 2,
Line 2, after "surface" delete "or" and substitute -- of --
Line 28, after "one" delete "and" and substitute -- end --
Line 35, delete "hag" and substittute -- has --
Line 40, delete "abutments" and substitute -- abutment; --
Line 49, after "types" delete "or" and substitute -- of --
Line 60, delete "go" and substitute -- so --

Signed and Sealed this

Twenty-first Day of August, 2001

*Attest:*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO. : 5,947,736  
DATED : September 7, 1999  
INVENTOR(S) : Donald A. Behrend Page 1 of 1

It is certified that error appears in the above-identified patent and that said Letters Patent is hereby corrected as shown below:

Column 1,  
Line 6, delete "roping" and substitute -- coping --  
Line 37, delete the commas (,) after "each" and "being"

Column 2,  
Line 2, after "surface" delete "or" and substitute -- of --  
Line 28, after "one" delete "and" and substitute -- end --  
Line 35, delete "hag" and substitute -- has --  
Line 40, delete "abutments" and substitute -- abutment:--  
Line 49, after "types" delete "or" and substitute -- of --  
Line 60, delete "go" and substitute -- so --

Signed and Sealed this

First Day of January, 2002

Attest:

JAMES E. ROGAN  
*Attesting Officer*   *Director of the United States Patent and Trademark Office*